United States Patent [19]
Benfey et al.

[11] Patent Number: 5,097,025
[45] Date of Patent: Mar. 17, 1992

[54] PLANT PROMOTERS

[75] Inventors: Philip N. Benfey, New York; Nam-Hai Chua, Scarsdale, both of N.Y.

[73] Assignee: The Rockefeller University, New York, N.Y.

[21] Appl. No.: 444,591

[22] Filed: Dec. 1, 1989

Related U.S. Application Data

[63] Continuation-in-part of Ser. No. 388,532, Aug. 1, 1989, abandoned.

[51] Int. Cl.$^5$ ............... C12N 15/11; C12N 15/82; C12N 15/83
[52] U.S. Cl. .................... 536/27; 435/320.1; 435/91; 435/172.1; 435/172.3; 935/6; 935/25; 935/30; 935/33; 935/41
[58] Field of Search ............... 435/320, 91, 172.1, 435/172.3, 320.1; 935/6, 25, 33, 30, 41; 536/27

[56] References Cited

PUBLICATIONS

Herr et al. (1986) Cell., vol. 45, pp. 461–470.
Schell (1987) Science, vol. 237, pp. 1176–1183.
Benfey et al. (1990) The EMBO Journal, vol. 9, No. 6, pp. 1677–1684.
O'Dell et al. (1985), Nature, vol. 313; pp. 810–812.
Benfey et al. (1989) Science, vol. 244, pp. 174–181.
Fang et al. (1989) The Plant Cell, vol. 1, pp. 141–150.
Kay et al. (1987) Science, vol. 236, pp. 1299–1302.
Benfey et al. (1990) The EMBO Journal, vol. 9, No. 6, pp. 1685–1696.
Philip N. Benfey et al., The CaMV35S enhancer contains at least two domains which can confer different developmental and tissue-specific expression patterns, EMBO J., (1989) 8:2195–2202.
Fumiaki Katagiri et al., Two tobacco DNA-binding proteins with homology to the nuclear factor CREB, Nature, (1989) 340:727–730.
Ferenc Nagy et al., The 5'-proximal region of the wheat Cab-1 gene contains a 268-bp enhancer-like sequence for phytochrome response, EMBO J., (1987) vol. 6, No. 9:2537–2542.
P. R. Sanders et al., Comparison of Cauliflower mosaic virus 35S and noplaine synthase promoters in transgenic plants, Nuc. Acids Res. (1987) 4:1543–1558.

Primary Examiner—Elizabeth C. Weimar
Assistant Examiner—Gary Benzion
Attorney, Agent, or Firm—Dennis R. Hoerner, Jr.; Thomas P. McBride; Howard C. Stanley

[57] ABSTRACT

Five subdomains of the CaMV35S promoter are provided that cause tissue specific and/or developmentally regulated expression of chimeric genes in plants. These subdomains act as promoters for use in transformed plant cells, seeds and transgenic plants. Some of the subdomains require fusion to domain A for expression. Subdomains B2, B3, B4, and B5 exhibit expression when fused to the minimal promoter sequence in mature plants whereas only B2 and B3 confer expression in seeds and only B2, B3 and B4 confer expression at the seedling stage of development. The combination of subdomains B4 and B5 confers expression at all stages of development as does the B1+TGACG motif combination when each combination is fused with the minimal promoter sequence. The nucleotide sequence and DNA molecule that function as the enhancers are provided.

12 Claims, 21 Drawing Sheets

Control Constructs
 B + A     B + -46     -46

Constructs Utilized

| #1  4xB1 + A       |              | #10 4xB1 + -46 |
|--------------------|--------------|----------------|
| #2  4xB2 + A       | #6  1xB2 + A | #11 4xB2 + -46 |
| #3  4xB3 + A       | #7  1xB3 + A | #12 4xB3 + -46 |
| #4  4xB4 + A       | #8  1xB4 + A | #13 4xB4 + -46 |
| #5  4xB5 + A       | #9  1xB5 + A | #14 4xB5 + -46 |

15 4x(B4+B5) + A
16 1x(B4+B5) + A        #19 4x(B4+B5) + -46
17 4x(B1+TG) + A        #20 1x(B4+B5) + -46
18 1x(B1+TG) + A        #21 4x(B1+TG) + -46

```
       -343
        |
5'-TGAGACTTTT CAACAAAGGG TAATATCCGG AAACCTCCTC

GGATTCCATT GCCCAGCTAT CTGTCACTTT ATTGTGAAGA TAGTGGAAAA

GGAAGGTGGC TCCTACAAAT GCCATCATTG CGATAAAGGA AAGGCCATCG

TTGAAGATGC CTCTGCCGAC AGTGGTCCCA AGATGGACC CCCACCCAC

GAGGAGCATC GTGGAAAAAG AAGACGTTCC AACCACGTCT TCAAAGCAAG
                          -90
                           |
TGGATTGATG TGAT ATCTCC ACTGACGTAA GGGATGACGC ACAATCCCAC

TATCCTTCGC AAGACCCTTC CTCTATATAA GGAAGTTCAT TTCATTTGGA
                  +8
                   |
GAGGACACGC TG-3'
```

FIGURE 1

Control Constructs
B + A           B + -46           -46

Constructs Utilized

1  4xB1 + A                              #10  4xB1 + -46
2  4xB2 + A        #6  1xB2 + A          #11  4xB2 + -46
3  4xB3 + A        #7  1xB3 + A          #12  4xB3 + -46
4  4xB4 + A        #8  1xB4 + A          #13  4xB4 + -46
5  4xB5 + A        #9  1xB5 + A          #14  4xB5 + -46

15  4x(B4+B5) + A
16  1x(B4+B5) + A                        #19  4x(B4+B5) + -46
17  4x(B1+TG) + A                        #20  1x(B4+B5) + -46
18  1x(B1+TG) + A                        #21  4x(B1+TG) + -46

```
Subdomain    B3 sequence
            HindIII  SalI  -208
1xB3+A  :A AGCTT GTCGAC CATCGTTGAAGAT GCCTCTGCC GACAGTGGTC
           T TCGAA CAGCTG GTAGCAACTTCTA CGGAGACGG CTGTCACCAG -155 XhoI          Linker
CCAAAGATGGACCCC CACCCAC C          TCGA GATC CCC
GGTTTCTACCTGGGG GTGGGTG G AGCT          CTAG GGG
Domain A
   ATCTCC ACTGACGTAA GGGATGACGC ACAATCCCAC TATCCTTCGC AAGACCCTTC
          CTCTATATAA GGAAGTTCAT TTCATTTGGA GAGGACACGC TG-3'

HindIII  SalI
4xB3+A  :A AGCTT GTCGAC CATCGTTGAAGAT GCCTCTGCC GACAGTGGTC
           T TCGAA CAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG XhoI          Linker
CCAAAGATGGACCCC CACCCAC C          TCGA GATC CCC
GGTTTCTACCTGGGG GTGGGTG G AGCT          CTAG GGG
Domain A
   ATCTCC ACTGACGTAA GGGATGACGC ACAATCCCAC TATCCTTCGC AAGACCCTTC
          CTCTATATAA GGAAGTTCAT TTCATTTGGA GAGGACACGC TG-3'

HindIII  SalI
4xB3+-46:A AGCTT GTCGAC CATCGTTGAAGAT GCCTCTGCC GACAGTGGTC
           T TCGAA CAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG SalI/XhoI
CCAAAGATGGACCCC CACCCAC CTCGAC CATCGTTGAAGAT GCCTCTGCC GACAGTGGTC
GGTTTCTACCTGGGG GTGGGTG GAGCTG GTAGCAACTTCTA CGGAGACGG CTGTCACCAG XhoI          Linker
CCAAAGATGGACCCC CACCCAC C          TCGA GATC
GGTTTCTACCTGGGG GTGGGTG G AGCT          CTAG
-46
       TCGC AAGACCCTTC CTCTATATAA GGAAGTTCAT TTCATTTGGA
           GAGGACACGC TG-3'
```

FIGURE 8 (a)

Subdomain     B2  +  -46 sequence

```
            SalI    XbaI    BamHI/XhoI   -155
4xB2+-46  :GTCGAC  TCTAGA  GGATCTCGAG  CGAGGAGCAT  CGTGGAAAAA
           CAGCTG  AGATCT  CCTAGAGCTC  GCTCCTCGTA  GCACCTTTTT

-108  HindIII/XhoI      -155
GAAGACGTTC  CAACCACGTC  TTCAAAGC  AAGCTT  CGAG      CGAGGAGCAT
CTTCTGCAAG  GTTGGTGCAG  AAGTTTCG  TTCGAA  GCTC      GCTCCTCGTA -108  HindIII/BamHI  SmaI/XbaI
CGTGGAAAAA  GAAGACGTTC  CAACCACGTC  TTCAAAGC  AAGCTGATC    CCCCTAGA
GCACCTTTTT  CTTCTCGAAG  GTTGGTGCAG  AAGTTTCG  TTCGACTAG    GGGGATCT BamHI/XhoI  -155                                                 -108
GGATCTCGAG  CGAGGAGCAT  CGTGGAAAAA  GAAGACGTTC  CAACCACGTC  TTCAAAGC
CCTAGAGCTC  GCTCCTCGTA  GCACCTTTTT  CTTCTGCAAG  GTTGGTGCAG  AAGTTTCG HindIII/XhoI    -155
AAGCTT  CGAG    CGAGGAGCAT  CGTGGAAAAA  GAAGACGTTC  CAACCACGTC
TTCGAA  GCTC    GCTCCTCGTA  GCACCTTTTT  CTTCTGCAAG  GTTGGTGCAG -108   HindIII/BamHI  SmaI/BamHI    XhoI    505 Linker
  TTCAAAGC  AAGCTGATC      CCCGATCC      C       TCGA  GATC
  AAGTTTCG  TTCGACTAG      GGGCTAGG      GAGCT         CTAG -46
      TCGC  AAGACCCTTC  CTCTATATAA  GGAAGTTCAT  TTCATTTGGA
            GAGGACACGC  TG-3'
```

FIGURE 8 (b)

| Subdomain | B2 + A sequence | | | | | |
|---|---|---|---|---|---|---|
| | HindIII | -155 | | | | |
| 1xB2+A: | AAGCTT CGAG | CGAGGAGCAT | CGTGGAAAAA | GAAGACGTTC | CAACCACGTC | |
| | TTCGAA GCTC | GCTCCTCGTA | GCACCTTTTT | CTTCTGAAG | GTTGGTGCAG | |

| | -108 | HindIII/BamHI | SmaI/HincII | XbaI | BamHI | XhoI |
|---|---|---|---|---|---|---|
| | TTCAAAGC | AAGCTGATC | CCCGAC | TCTAGA | GGATCC | C |
| | AAGTTTCG | TTCGACTAG | GGGCTG | AGATCT | CCTAGG | G AGCTC |

505 Linker
TCGA GATC CCC
 CTAG GGG

Domain A
 ATCTCC ACTGACGTAA GGGATGACGC ACAATCCCAC TATCCTTCGC AAGACCCTTC
  CTCTATATAA GGAAGTTCAT TTCATTTGGA GAGGACACGC TG-3'

| | SalI | XbaI | BamHI/XhoI | -155 | |
|---|---|---|---|---|---|
| 4xB2+A: | GTCGAC | TCTAGA | GGATCTCGAG | CGAGGAGCAT | CGTGGAAAAA |
| | CAGCTG | AGATCT | CCTAGAGCTC | GCTCCTCGTA | GCACCTTTTT |

| | | -108 | HindIII/XhoI | -155 | |
|---|---|---|---|---|---|
| GAAGACGTTC | CAACCACGTC | TTCAAAGC | AAGCTT CGAG | CGAGGAGCAT | |
| CTTCTGCAAG | GTTGGTGCAG | AAGTTTCG | TTCGAA GCTC | GCTCCTCGTA | |

| | | | -108 | HindIII/BamHI | SmaI/XbaI |
|---|---|---|---|---|---|
| CGTGGAAAAA | GAAGACGTTC | CAACCACGTC | TTCA AAGC | AAGCTGATC | CCCCTAGA |
| GCACCTTTTT | CTTCTGAAG | GTTGGTGCAG | AAGT TTCG | TTCGACTAG | GGGGATCT |

| BamHI/XhoI | -155 | | | | -108 |
|---|---|---|---|---|---|
| GGATCTCGAG | CGAGGAGCAT | CGTGGAAAAA | GAAGACGTTC | CAACCACGTC | TTCAAAGC |
| CCTAGAGCTC | GCTCCTCGTA | GCACCTTTTT | CTTCTGCAAG | GTTGGTGCAG | AAGTTTCG |

| HindIII /XhoI | -155 | | | |
|---|---|---|---|---|
| AAGCTT CGAG | CGAGGAGCAT | CGTGGAAAAA | GA AGACGTTC | CAACCACGTC |
| TTCGAA GCTC | GCTCCTCGTA | GCAC CTTTTT | CT TCTGCAAG | GTTGGTGCAG |

| | -108 | HindIII/BamHI | SmaI/BamHI | XhoI | 505 Linker |
|---|---|---|---|---|---|
| | TTCAAAGC | AAGCTGATC | CCCGATCC | C | TCGA GATC CCC |
| | AAGTTTCG | TTCGACTAG | GGGCTAGG | GAGCT | CTAG GGG |

Domain A
 ATCTCC ACTGACGTAA GGGATGACGC ACAATCCCAC TATCCTTCGC AAGACCCTTC
  CTCTATATAA GGAAGTTCAT TTCATTTGGA GAGGACACGC TG-3'

FIGURE 8 (c)

Subdomain    B1  sequence

```
            HindIII SalI -108              -91    -87
4xB1+A  : A AGCTT GTCGAC AAGTGGATTGATG  TGAT ATCTAAGTGGATTGATG TGATATCT
          T TCGAA CAGCTG TTCACCTAACTAC  ACTA TAGATTCACCTAACTAC ACTATAGA XhoI      Linker
AAGTGGATTGATG TGATATCT AAGTGGATTGATG TGAT  C        TCGA GATC CCC
TTCACCTAACTAC ACTATAGA TTCACCTAACTAC ACTA  G AGCT        CTAG GGG
```

Domain A
```
    ATCTCC ACTGACGTAA GGGATGACGC ACAATCCCAC TATCCTTCGC AAGACCCTTC
           CTCTATATAA GGAAGTTCAT TTCATTTGGA GAGGACACGC TG-3'
```

```
          HindIII SalI
4xB1+-46 :A AGCTT GTCGAC AAGTGGATTGATG  TGAT ATCTAAGTGGATTGATG TGATATCT
          T TCGAA CAGCTG TTCACCTAACTAC  ACTA TAGATTCACCTAACTAC ACTATAGA XhoI      Linker
AAGTGGATTGATG TGATATCT AAGTGGATTGATG TGAT  C        TCGA GATC
TTCACCTAACTAC ACTATAGA TTCACCTAACTAC ACTA  G AGCT        CTAG -46
    TCGC   AAGACCCTTC CTCTATATAA GGAAGTTCAT TTCATTTGGA
           GAGGACACGC TG-3'
```

FIGURE 8 (d)

Subdomain    B4   sequence

```
              HindIII    -301
1xB4+A  :  AAGCTT GGGC  ATTCCATTGC  CCAGCTATCT  GTCACTTTAT  TGTGAAGATA
           TTCGAA CCCG  TAAGGTAACG  GGTCGATCTA  CTGTGAAATA  ACTCTTCTAT -208
GTGGAAAAGG  AAGGTGGCTC  CTACAAATGC  CATCATTGCG  ATAAAGGAAA  GGCC
CTCCTTTTCC  TTCCACCGAT  GATGTTTACG  GTAGTAACGC  TATTTCCTTT  CCGG
```

Sa1I Linker      505     Linker
CGG              TCGA    GATC CCC
GCCAGCT                  CTAG GGG Domain A
```
    ATCTCC ACTGACGTAA GGGATGACGC ACAATCCCAC TATCCTTCGC AAGACCCTTC
           CTCTATATAA GGAAGTTCAT TTCATTTGGA GAGGACACGC TG-3'
```

FIGURE 8 (e)

Subdomain    B4 sequence

```
         HindIII   PstI    HincII/EcoRV  BglII   XhoI      EcoRI/HindIII
4xB4+A :AAGCTT GGGCTGCAG GTC ATC       AGATCT CTCGAG GAATTAGCTT
        TTCGAA CCCGACGTC CTG TAG       TCTAGA GAGCTC CTTAATCGAA GGGC ATTCCATTGC CCAGCTATCT GTCACTTTAT TGTGAAGATA
       CCCG TAAGGTAACG GGTCGATCTA CTGTGAAATA ACTCTTCTAT
                                                              -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG
    SalI/XhoI   BamHI/BglII
CGG TCGA G        GGATC T          CTCGAG GAATTAGCTT
GCC AGCT C        CCTAG A          GAGCTC CTTAATCGAA GGGC ATTCCATTGC CCAGCTATCT GTCACTTTAT TGTGAAGATA
CCCG TAAGGTAACG GGTCGATCTA CTGTGAAATA ACTCTTCTAT
                                                              -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG
    SalI/XhoI   BamHI/BglII
CGG TCGA G        GGATC    T       CTC GAG GAATTAGCTT
GCC AGCT C        CCTAG    A       GAG CTC CTTAATCGAA GGGC ATTCCATTGC CCAGCTATCT GTCACTTTAT TGTGAAGATA
CCCG TAAGGTAACG GGTCGATCTA CTGTGAAATA ACTCTTCTAT
                                                              -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG
    SalI/XhoI   BamHI/BglII
CGG TCGA G        GGATC T          CTCGAG GAATTAGCTT
GCC AGCT C        CCTAG A          GAGCTC CTTAATCGAA GGGC ATTCCATTGC CCAGCTATCT GTCACTTTAT TGTGAAGATA
CCCG TAAGGTAACG GGTCGATCTA CTGTGAAATA ACTCTTCTAT
                                                              -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG
    SalI/XhoI  BamHI         SmaI    SacI       505 Linker
CGG TCGA G     GGATCC        CCCGGG GAGCT       CTCGA GATC CCC
GCC AGCT C     CCTAGG        GGGCCC C           TCGA GAGCT CTAG GGG
Domain A
       ATCTCC ACTGACGTAA GGGATGACGC ACAATCCCAC TATCCTTCGC AAGACCCTTC
              CTCTATATAA GGAAGTTCAT TTCATTTGGA GAGGACACGC TG-3'
```

FIGURE 8 (f)

Subdomain    B4 sequence

```
            HindIII    PstI    HincII/EcoRV   BglII    XhoI    EcoRI/HindIII
4xB4+-46: AAGCTT  GGGCTGCAG  GTC ATC       AGATCT   CTCGAG  GAATTAGCTT
          TTCGAA  CCCGACGTC  CTG TAG       TCTAGA   GAGCTC  CTTAATCGAA GGGC ATTCCATTGC CCAGCTATCT GTCACTTTAT TGTGAAGATA
          CCCG TAAGGTAACG GGTCGATCTA CTGTGAAATA ACTCTTCTAT
                                                                      -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI    BamHI/BglII
CGG TCGA G      GGATC   T         CTCGAG GAATTAGCTT
GCC AGCT C      CCTAG   A         GAGCTC CTTAATCGAA GGGC ATTCCATTGC CCAGCTATCT  GTCACTTTAT TGTGAAGATA
CCCG TAAGGTAACG GGTCGATCTA  CTGTGAAATA ACTCTTCTAT
                                                                      -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI    BamHI/BglII
CGG TCGA G      GGATC   T         CTC GAG GAATTAGCTT
GCC AGCT C      CCTAG   A         GAG CTC CTTAATCGAA GGGC ATTCCATTGC CCAGCTATCT  GTCACTTTAT TGTGAAGATA
CCCG TAAGGTAACG GGTCGATCTA  CTGTGAAATA ACTCTTCTAT
                                                                      -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI    BamHI/BglII
CGG TCGA G      GGATC   T         CTCGAG GAATTAGCTT
GCC AGCT C      CCTAG   A         GAGCTC CTTAATCGAA GGGC ATTCCATTGC CCAGCTATCT  GTCACTTTAT TGTGAAGATA
CCCG TAAGGTAACG GGTCGATCTA  CTGTGAAATA ACTCTTCTAT
                                                                      -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI  BamHI         SmaI     SacI      505 Linker
CGG TCGA G    GGATCC        CCCGGG GAGCT       CTCGA GATC
GCC AGCT C    CCTAGG        GGGCCC C      TCGA GAGCT CTAG
-46
      TCGC AAGACCCTTC CTCTATATAA GGAAGTTCAT TTCATTTGGA
             GAGGACACGC TG-3'
```

FIGURE 8 (g)

```
Subdomain     B5 sequence
           HindIII     SalI    -343
1xB5+A  :A AGCTT    GTCGAC  TGAGACTTTT CAACAAAGGG TAATATCCGG AAACCTCCTC
         T TCGAA    CAGCTG  ACTCTGAAAA GTTGTTTCCC ATTATAGGCC TTTGGAGGAG -299 XhoI         Linker
GGATT C       TCGA TAGC CCC
CCTAA GAGCT        CTAG GGG Domain A
     ATCTCC ACTGACGTAA GGGATGACGC ACAATCCCAC TATCCTTCGC AAGACCCTTC
            CTCTATATAA GGAAGTTCAT TTCATTTGGA GAGGACACGC TG-3'

HindIII     SalI    -343
4xB5+A  :A AGCTT    GTCGAC  TGAGACTTTT CAACAAAGGG TAATATCCGG AAACCTCCTC
         T TCGAA    CAGCTG  ACTCTGAAAA GTTGTTTCCC ATTATAGGCC TTTGGAGGAG -299
GGATT C TCGAC TGAGACTTTT CAACAAAGGG TA ATATCCGG AAACCTCCTC GGATT
CCTAA G AGCTG ACTCTGAAAA GTTGTTTCCC AT TATAGGCC TTTGGAGGAG CCTAA C TCGAC TGAGACTTTT CAACAAAGGG TAATATCCGG AAACCTCCTC
G AGCT  ACTCTGAAAA GTTGTTTCCC ATTATAGGCC TTTGGAGGAG GGATT C TCGAC TGAGACTTTT CAACAAAGGG TA ATATCCGG AAACCTCCTC GGATT
CCTAA G AGCTG ACTCTGAAAA GTTGTTTCCC AT TATAGGCC TTTGGAGGAG CCTAA XhoI       Linker
C       TCGA GATC CCC
GAGCT        CTAG GGG Domain A
     ATCTCC ACTGACGTAA GGGATGACGC ACAATCCCAC TATCCTTCGC AAGACCCTTC
            CTCTATATAA GGAAGTTCAT TTCATTTGGA GAGGACACGC TG-3'

HindIII     SalI    -343
4xB5+-46:A AGCTT    GTCGAC  TGAGACTTTT CAACAAAGGG TAATATCCGG AAACCTCCTC
         T TCGAA    CAGCTG  ACTCTGAAAA GTTGTTTCCC ATTATAGGCC TTTGGAGGAG -299
GGATT C TCGAC TGAGACTTTT CAACAAAGGG TA ATATCCGG AAACCTCCTC GGATT
CCTAA G AGCTG ACTCTGAAAA GTTGTTTCCC AT TATAGGCC TTTGGAGGAG CCTAA C TCGAC TGAGACTTTT CAACAAAGGG TAATATCCGG AAACCTCCTC
G AGCT  ACTCTGAAAA GTTGTTTCCC ATTATAGGCC TTTGGAGGAG GGATT C TCGAC TGAGACTTTT CAACAAAGGG TA ATATCCGG AAACCTCCTC GGATT
CCTAA G AGCTG ACTCTGAAAA GTTGTTTCCC AT TATAGGCC TTTGGAGGAG CCTAA XhoI       Linker    -46
C       TCGA GATC TCGCAAGACC CTTCCTCTAT ATAAGGAAGT TTCATTTCAT
GAGCT        CTAG +8 HindIII
TTGGAGAGGA CACGCTGAAG CTT
```

FIGURE 8 (h)

Subdomain B1+TG sequence

```
               HindIII  SalI  -108                                              -72
1x(B1+TG)+A: A AGCTT GTCGAC AAGTGGATTGATG TGATATC TCCACTG ACGTAAGGG
               T TCGAA CAGCTG TTCACCTAACTAC ACTATAG AGGTGAC TGCATTCCC Xho I       505 Linker
C           TCGA GATC CCC
GAGCT            CTAG GGG
```

Domain A
```
    ATCTCC ACTGACGTAA GGGATGACGC ACAATCCCAC TATCCTTCGC AAGACCCTTC
           CTCTATATAA GGAAGTTCAT TTCATTTGGA GAGGACACGC TG-3'

HindIII SalI  -108                                               -72
4x(B1+TG)+A: A AGCTT GTCGAC AAGTGGATTGATG TGATATC TCCACTG ACGTAAGGG
               T TCGAA CAGCTG TTCACCTAACTAC ACTATAG AGGTGAC TGCATTCCC XhoI/SalI -108                                    -72 XhoI/SalI
CTCGAC   AAGTGGATTGATG TGATATC TCCACTG ACGTAAGGG CTCGAC AAGTGGATTGATG
GTGCAG   TTCACCTAACTAC ACTATAG AGGTGAC TGCATTCCC GTGCAG TTCACCTAACTAC Xho I / SalI
TGATATC TCCACTG ACGTAAGGG CTCGAC AAGTGGATTGATG TGATATC TCCACTG
ACTATAG AGGTGAC TGCATTCCC GTGCAG TTCACCTAACTAC ACTATAG AGGTGAC XhoI       505 Linker
ACGTAAGGG  C        TCGA GATC CCC
TGCATTCCC  GAGCT         CTAG GGG
```

Domain A
```
    ATCTCC ACTGACGTAA GGGATGACGC ACAATCCCAC TATCCTTCGC AAGACCCTTC
           CTCTATATAA GGAAGTTCAT TTCATTTGGA GAGGACACGC TG-3'

HindIII SalI  -108                                              -72
4x(B1+TG)+-46: A AGCTT GTCGAC AAGTGGATT GATG TGATATC TCCACTG ACGTAAGGG
                T TCGAA CAGCTG TTCACCTAA CTAC ACTATAG AGGTGAC TGCATTCCC XhoI/SalI                                            XhoI/SalI
CTCGAC   AAGTGGATTGATG TGATATC TCCACTG  ACGTAAGGG  CTCGAC AAGTGGATTGATG
GTGCAG   TTCACCTAACTAC ACTATAG AGGTGAC  TGCATTCCC  GTGCAG TTCACCTAACTAC Xho I / SalI
TGATATC TCCACTG ACGTAAGGG CTCGAC AAGTGGATTGATG TGATATC TCCACTG
ACTATAG AGGTGAC TGCATTCCC GTGCAG TTCACCTAACTAC ACTATAG AGGTGAC Xho I      505 Linker
ACGTAAGGG  C        TCGA GATC
TGCATTCCC  GAGCT         CTAG
-46
    TCGC AAGACCCTTC CTCTATATAA GGAAGTTCAT TTCATTTGGA
         GAGGACACGC TG-3'
```

FIGURE 8 (i)

Subdomains    B4+B5 sequence

```
                   HindIII    PstI  SalI/XhoI   -343
1x(B4+B5)+A  :A AGCTT  GGGCTGCAG  GTCGAG  TGAGACTTTT  CAACAAAGGG  TAATATCCGG
              T TCGAA  CCCGACGTC  CAGCTG  ACTCTGAAAA  GTTGTTTCCC  ATTATAGGCC AAACCTCCTC  GGATTCCATTGC  CCAGCTATCT  GTCACTTTAT  TGTGAAGATA
TTTGGAGGAG  CCTAAGGTAACG  GGTCGATCTA  CAGTGAAATA  ACTCTTCTAT
```

-208
```
GTGGAAAAGG  AAGGTGGCTC  CTACAAATGC  CATCATTGCG  ATAAAGGAAA  GGCC
CTCCTTTTCC  TTCCACCGAT  GATGTTTACG  GTAGTAACGC  TATTTCCTTT  CCGG
```

SalI        505 Linker
```
G       TCGA  GATC  CCC
CAGCT         CTAG  GGG
```

Domain A
```
   ATCTCC  ACTGACGTAA  GGGATGACGC  ACAATCCCAC  TATCCTTCGC  AAGACCCTTC
           CTCTATATAA  GGAAGTTCAT  TTCATTTGGA  GAGGACACGC  TG-3'
```

FIGURE 8 (j)

Subdomains B4+B5 sequence

```
              HindIII    PstI     SalI/XhoI  -343
4x(B4+B5)+A:A AGCTT  GGGCTGCAG GTCGAG TGAGACTTTT CAACAAAGGG TAATATCCGG
             T TCGAA CCCGACGTC CAGCTG ACTCTGAAAA GTTGTTTCCC ATTATAGGCC AAACCTCCTC GGATTCCATTGC CCAGCTATCT GTCACTTTAT TGTGAAGATA
TTTGGAGGAG CCTAAGGTAACG GGTCGATCTA CTGTGAAATA ACTCTTCTAT
                                                                  -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI  -343
GTCGAG     TGAGACTTTT CAACAAAGGG TAATATCCGG
CAGCTG     ACTCTGAAAA GTTGTTTCCC ATTATAGGCC AAACCTCCTC GGATTCCATTGC CCAGCTATCT GTCACTTTAT TGTGAAGATA
TTTGGAGGAG CCTAAGGTAACG GGTCGATCTA CTGTGAAATA ACTCTTCTAT
                                                                  -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/PstI  -343
GTCGA  G   GTCGAG TGAGACTTTT CAACAAAGGG  TAATATCCGG
CAGCT  C   CAGCTG ACTCTGAAAA GTTGTTTCCC  ATTATAGGCC AAACCTCCTC GGATTCCATTGC CCAGCTATCT GTCACTTTAT TGTGAAGATA
TTTGGAGGAG CCTAAGGTAACG GGTCGATCTA CTGTGAAATA ACTCTTCTAT
                                                                  -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/ShoI  -343
GTCGAG     TGAGACTTTT CAACAAAGGG TAATAT CCGG
CAGCTG     ACTCTGAAAA GTTGTTTCCC ATTATA GGCC AAACCTCCTC GGATTCCATTGC CCAGCTATCT GTCACTTTAT TGTGAAGATA
TTTGGAGGAG CCTAAGGTAACG GGTCGATCTA CTGTGAAATA ACTCTTCTAT
                                                                  -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI       505 Linker
G      TCGA GATC CCC
CAGCT       CTAG GGG Domain A
    ATCTCC ACTGACGTAA GGGATGACGC ACAATCCCAC TATCCTTCGC AAGACCCTTC
           CTCTATATAA GGAAGTTCAT TTCATTTGGA GAGGACACGC TG-3'
```

FIGURE 8 (k)

```
Subdomains      B4+B5 +  -46

HindIII  PstI  SalI/XhoI  - 343
1x(B4+B5)+-46:A AGCTT  GGGCTGCAG GTCGAG  TGAGACTTTT CAACAAAGGG TAATATCCG
              T TCGAA  CCCGACGTC CAGCTG  ACTCTGAAAA GTTGTTTCCC ATTATAGGC AAACCTCCTC GGATTCCATTGC CCAGCTATCT GTCACTTTAT TGTGAAGATA
TTTGGAGGAG CCTAAGGTAACG GGTCGATCTA CTGTGAAATA ACTCTTCTAT -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI        505 Linker
G      TCGA  GATC
CAGCT        CTAG -46
       TCGC AAGACCCTTC CTCTATATAA GGAAGTTCAT TTCATTTGGA
            GAGGACACGC TG-3'
```

FIGURE 8 (I)

Subdomains B4+B5 sequence

```
                 HindIII   PstI   SalI/XhoI  -343
4x(B4+B5)+-46:A AGCTT GGGCTGCAG GTCGAG TGAGACTTTT CAACAAAGGG TAATATCCG
              T TCGAA CCCGACGTC CAGCTG ACTCTGAAAA GTTGTTTCCC ATTATAGGC AAACCTCCTC GGATTCCATT GC CCAGCTATCT GTCACTTTAT TGTGAAGATA
TTTGGAGGAG CCTAAGGTAACG GGTCGATCTA CTGTGAAATA ACTCTTCTAT
                                                        -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI  -343
GTCGAG     TGAGACTTTT CAACAAAGGG TAATATCCGG
CAGCTG     ACTCTGAAAA GTTGTTTCCC ATTATAGGCC AAACCTCCTC GGATTCCATT GC CCAGCTATCT GTCACTTTAT TGTGAAGATA
TTTGGAGGAG CCTAAGGTAACG GGTCGATCTA CTGTGAAATA ACTCTTCTAT
                                                        -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/PstI  -343
GTCGA  G   GTCGAG TGAGACTTTT CAACAAAGGG TAATATCCGG
CAGCT  C   CAGCTG ACTCTGAAAA GTTGTTTCCC ATTATAGGCC AAACCTCCTC GGATTCCATT GC CCAGCTATCT GTCACTTTAT TGTGAAGATA
TTTGGAGGAG CCTAAGGTAACG GGTCGATCTA CTGTGAAATA ACTCTTCTAT
                                                        -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI/XhoI  -343
GTCGAG     TGAGACTTTT CAACAAAGGG TAATATCCGG
CAGCTG     ACTCTGAAAA GTTGTTTCCC ATTATAGGCC AAACCTCCTC GGATTCCATT GC CCAGCTATCT GTCACTTTAT TGTGAAGATA
TTTGGAGGAG CCTAAGGTAACG GGTCGATCTA CTGTGAAATA ACTCTTCTAT
                                                        -208
GTGGAAAAGG AAGGTGGCTC CTACAAATGC CATCATTGCG ATAAAGGAAA GGCC
CTCCTTTTCC TTCCACCGAT GATGTTTACG GTAGTAACGC TATTTCCTTT CCGG SalI       505 Linker
G          TCGA GATC
CAGCT           CTAG -46
      TCGC AAGACCCTTC CTCTATATAA GGAAGTTCAT TTCATTTGGA
           GAGGACACGC TG-3'
```

FIGURE 8 (m)

PLANT PROMOTERS

This is a continuation-in-part of our co-pending application having Ser. No. 07/388,532, now abandoned filed on Aug. 1, 1989.

BACKGROUND OF THE INVENTION

This invention relates in general to promoters for use in transgenic plants and more particularly to the tissue-specific expression and synergistic interactions of subdomains of the 35S promoter of cauliflower mosaic virus (CaMV).

Through the use of recombinant DNA technology and genetic engineering, it has become possible to introduce desired DNA sequences or genes into cells to allow for the expression of proteins of interest. This technology has been applied to plants to provide plants having unique characteristics. In order to obtain adequate expression of a gene inserted into a plant cell, a promoter sequence operable in plant cells is normally required. The 35S promoter of cauliflower mosaic virus (CaMV35S) is one such promoter and acts as a strong constitutive promoter in most organs of transgenic plants (Odell et al., 1985; Jensen et al., 1986; Jefferson et al., 1987; Kay et al., 1987; Sanders et al., 1987). The upstream region from −343 to −46 (upstream of the "TATA" box nucleotides) of the CaMV35S promoter has been shown to function in an orientation and distance independent manner (Fang et al., 1989; Nagy et al., 1987). It has also been previously shown that this enhancer is composed of at least two domains able to confer tissue-specific and developmentally regulated expression in transgenic plants (Benfey et al., 1989). One of the domains (−90 to +8) has been termed domain A (which also contains the TATA region from −46 to +8) and is able to confer expression principally in root tissue (Benfey et al., 1989). A sequence motif of a tandem repeat of TGACG has been identified within domain A that binds a factor found in nuclear extracts from tobacco (Lam et al., 1989). A cDNA clone for a factor that binds to this motif has also been isolated (Katagiri et al., 1989). The level of the RNA that hybridizes to this cDNA is 5 to 10 fold higher in the root than in the leaf (Katagiri et al., 1989). Domain A, therefore, appears to be able to confer expression in root tissue because it contains a sequence motif that interacts with a factor that is found predominantly in root. Previous work has also indicated that domain A may play a role in potentiating transcription when associated with other cis-elements. In particular, domain A has been shown to be able to interact synergistically with a region further upstream to potentiate transcription in leaf (Fang et al., 1989). The second domain (containing nucleotides −343 to −90) has been termed domain B and has been shown to confer expression in most cell types of leaf and stem as well as in vascular tissue of the root (Benfey et al., 1989).

It would be advantageous to the development and use of transgenic plants to be able to direct tissue-specific expression of genes inserted in these plants. While the general tissue targets of domain A and domain B of the CaMV35S promoter are known, defining the tissue-specific and developmentally regulated expression patterns conferred by isolated subdomains of the CaMV35S promoter, if such exist, would provide greater insight into the utility of the promoter in transgenic plants.

It is therefore a primary object of the present invention to provide the tissue-specific and/or developmentally regulated expression of chimeric plant genes, by the use of novel promoters comprising subdomains of the CaMV35S promoter.

It is another object of the present invention to provide novel promoters for use in transformed plant cells, transgenic plants and seeds that are comprised of a subdomain or combination of subdomains from the CaMV35S promoter.

BRIEF DESCRIPTION OF THE DRAWINGS

FIG. 1 represents the nucleotide sequence (−343 to +8) for the CaMV35S promoter.

FIG. 8(a) illustrates the nucleotide sequences of the B3 subdomain containing constructs.

FIG. 8(b) illustrates the nucleotide sequence of the construct containing the tetramer of the B2 subdomain when fused with the minimal promoter (−46 to +8) of CaMV35S.

FIG. 8(c) illustrates the nucleotide sequences of the B2 subdomain containing constructs when fused with domain A.

FIG. 8(d) illustrates the nucleotide sequences of the B1 subdomain containing constructs.

FIG. 8(e) illustrates the nucleotide sequence of the B4 monomer subdomain containing construct when fused with domain A.

FIG. 8(f) illustrates the nucleotide sequence of the B4 tetramer subdomain containing construct when fused with domain A.

FIG. 8(g) illustrates the nucleotide sequence of the B4 tetramer subdomain containing construct when fused with the minimal promoter (−46 to +8) of CaMV35S.

FIG. 8(h) illustrates the nucleotide sequences of the B5 subdomain containing constructs.

FIG. 8(i) illustrates the nucleotide sequences of the B1 subdomain plus TGACG motif containing constructs.

FIG. 8(j) illustrates the nucleotide sequence of the B4 plus B5 monomer subdomain containing construct when fused with domain A.

FIG. 8(k) illustrates the nucleotide sequence of the B4 plus B5 tetramer subdomain containing construct when fused with domain A.

FIG. 8(l) illustrates the nucleotide sequence of the B4 plus B5 monomer subdomain containing construct when fused with the minimal promoter (−46 to +8) of CaMV35S.

FIG. 8(m) illustrates the nucleotide sequence of the B4 plus B5 tetramer subdomain containing construct when fused with the minimal promoter (−46 to +8) of CaMV35S.

SUMMARY OF THE INVENTION

The present invention provides five subdomains of domain B of the CaMV35S promoter where each subdomain is able to confer a different tissue specific and developmentally regulated expression pattern. The subdomains are denoted as B1, B2, B3, B4 and B5. Expression of all of the subdomains is readily detectable when fused with domain A in seeds, seedlings and mature plants. Subdomains B2, B3 and the combination constructs of subdomains B4 plus B5 and B1 plus the TGACG motif also exhibit expression when fused to the minimal promoter sequence (−46 to +8) in seeds and seedlings. Subdomain B4 confers expression when fused to the minimal promoter sequence at the seedling stage. Furthermore, subdomains B2, B3, B4 and B5 confer distinct expression patterns in mature plants when fused with only the minimal promoter sequence.

DETAILED DESCRIPTION OF THE INVENTION

It has been discovered that domain B of the CaMV35S promoter can be divided into five discreet subdomains that each exhibit tissue-specific and developmentally regulated expression patterns. It has also been discovered that in order to detect the expression patterns described here from any of the individual subdomains, except B2, in seeds and seedlings, the subdomain needs to be fused to domain A. Domain B has been found to confer expression when fused to the minimal promoter. Expression from B2, B3 and a combination of two of the subdomains (B4 and B5) is detectable in seeds and seedlings when fused to the minimal promoter sequence. In mature plants, subdomains B2, B3, B4 and B5 show a distinct expression pattern when fused to the minimal promoter sequence. The presence of the minimal promoter sequence alone confers no detectable expression of the reporter GUS gene.

Figure 2:
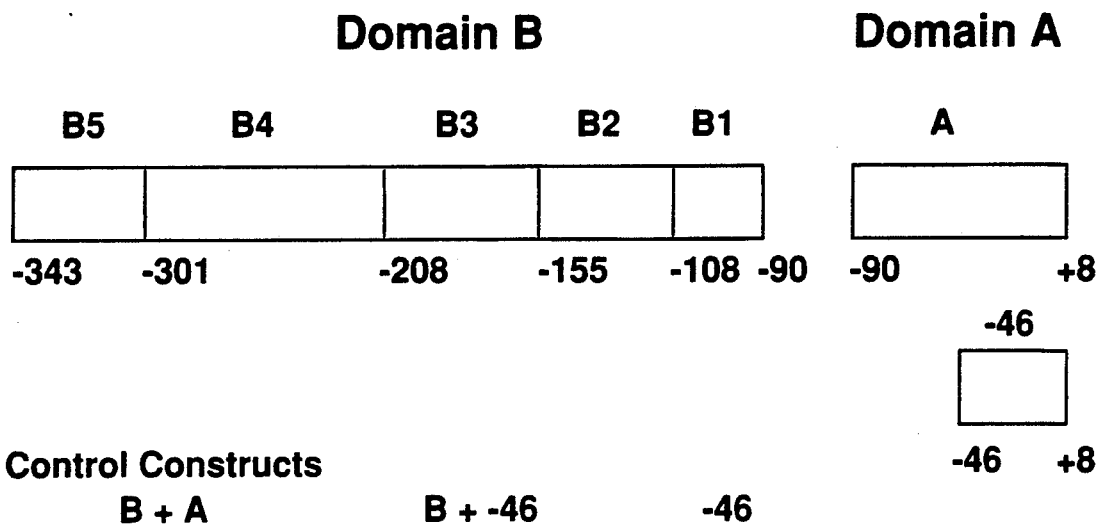
FIG. 2 represents the domains A and B of the CaMV35S promoter with the five subdomains of domain B and the breakpoints of the subdomains as well as the minimal promoter fragment (−46 to +8) and a list of the constructs utilized in this invention.

In order to determine the effects of the subdomains, domain B (−343 to −90) of the 35S promoter was divided into five subdomains as shown in FIG. 2. The breakpoints were approximately the same as those used in a previous deletion analysis (Fang et al., 1989). The entire nucleotide sequence for CaMV35S (−343 to +8) is shown in FIG. 1. The subdomains were fused as monomers or tetramers to domain A (−90 to +8) and as tetramers to the minimal promoter fragment (−46 to +8) (FIG. 2). Subdomain B1 was fused only as a tetramer to domain A. Control constructs include the minimal promoter alone (−46 to +8), domain B fused to the minimal promoter and domain B fused to domain A which re-assembles the complete CaMV35S promoter (−343 to +8) except for the presence of linker sequences between the two domains (FIG. 2). In addition, two combinations of subdomains were analyzed. Subdomains B4 and B5 (−343 to −208) and subdomain B1 with one TGACG sequence motif (−105 to −72) were fused as monomers or tetramers to domain A and to the minimal promoter. The orientation dependence of subdomain 2 was also analyzed. The β-glucuronidase (GUS) coding sequence (Jefferson et al., 1987) was present in all constructs as a transcriptional fusion gene. These constructs were introduced into tobacco and expression was analyzed at different developmental stages. At least six independent transformants were analyzed for each construct.

Promoter Fragment Constructs

As described above, the CaMV35S promoter has been divided into two fragments, domain A (nucleotides −90 to +8) and domain B (nucleotides −343 to −90). Domain B was further divided into five subdomains: B1 (nucleotides −108 to −90), B2 (nucleotides −155 to −108), B3 (nucleotides −208 to −155), B4 (nucleotides −301 to −208), and B5 (nucleotides −343 to −301). It was found that these subdomains confer different expression patterns in transgenic plants. It was further found that B2, B3, B4 and B5 conferred signicant expression when fused with the minimal promoter fragment.

The construct containing domain A into which the subdomains were inserted is the same as X-GUS-90 described previously (Benfey and Chua, 1989). This construct was made by fusion of the 35S promoter fragment A (−90 to +8) to the β-Glucuronidase coding region from pRAJ260 (Jefferson et al. 1987) which in turn was fused to the pea rbcS 3C 3′ end (this fusion product had a BamHI site at the 5′ end and an EcoRI site at the 3′ end) and inserted into the polylinker between the BglII site and the EcoRI site of the binary vector pMON505. The entire 35S promoter fragment (−941 to +8) transcriptionally fused to the CAT coding sequence with a pea rbcS-E9 3′ end was then inserted in the BglII linkers at the HpaI site of pMON505. The minimal promoter construct (X-GUS-46) was made in essentially the same manner except that the fragment from −46 to +8 was synthesized as complementary oligonucleotides with a HindIII site at the 3′ end and a BglII site at the 5′ end. This was subcloned, sequenced for accuracy and then fused to the GUS coding region. The HindIII site was filled in with Klenow enzyme. The BglII (5′), EcoRI (3′) fragment containing the 35S minimal promoter sequence (−46 to +8) fused to the GUS coding sequence with a 3′ end from the pea rbcS 3C gene was then inserted between the BglII and EcoRI sites of the polylinker of pMON505 (Horsch and Klee, 1986). A construct containing the 35S promoter (−941 to +8) fused to the chloramphenicol acetyl transferase (CAT) coding sequence with a 3′ end from the pea rbcS-E9 gene was inserted as a blunt end ligation into the HpaI site 4 kb away from the GUS construct. (CAT activity was routinely measured to confirm that all plants were transformed.)

Two subdomains (B3 and B5) were synthesized as complementary oligonucleotides with a HindIII site followed by a SalI site at the 5′ end and an XhoI site at the 3′ end to allow for multimerization. Tetramers were made by ligation of monomer containing plasmid cut with HindIII and SalI, and fragment cut with HindIII and XhoI, then repetition of the process. Monomers and tetramers were inserted between the HindIII (5′) and XhoI (3′) sites in X-GUS-90 and in X-GUS-46. The B1 subdomain was synthesized directly as a tetramer with a HindIII site at the 5′ end and an XhoI site at the 3′ end and inserted between the HindIII and XhoI sites of X-GUS-90 and X-GUS-46.

The B2 subdomain was synthesized as complementary oligonucleotides with XhoI at the 5′ end and HindIII at the 3′ end. The sites were filled in and blunt end ligated into a filled in BamHI site of pEMBL 13. A head to tail dimer resulted from this ligation with SalI and XbaI sites at the 5' end, a HindIII site (recreated by the blunt end ligation to the filled in XhoI site) at the 3' end of the first monomer and XhoI, SmaI and SacI sites at the 3' end of the dimer. The tetramer was made by cutting with XbaI, filling in the site, then with SacI. This fragment was cloned into the plasmid containing the dimer between the SmaI site and the SacI site. The tetramer was cloned into the XhoI site of X-GUS-46 and X-GUS-90 as a SalI (5'), XhoI (3') fragment. This ligation resulted in insertion in both orientations. The monomer was isolated as a HindIII (5'), XhoI (3') fragment and inserted between these sites in the two expression vectors.

The B4 subdomain was cut from a 3' deletion derivative of the 35S promoter described in Fang et al. (1989) from −343 to −208 by cleavage with HinfI at nucleotide −301 and filled in with Klenow enzyme. The fragment from −301 to −208 was ligated into pEMBL 13 between a PstI site treated with T4 DNA polymerase at the 5' end and a SalI site at the 3' end. This was then subcloned into a derivative of pEMBL 13 that contains a BglII site in such a way that the BglII was at the 5' end and the BamHI site was at the 3' end. This was multimerized by cutting with BglII and BamHI and ligation of the fragment at high concentration. The monomer and tetramer were inserted into the expression vectors between the HindIII site (5') and the SacI site (3').

The combination of B4 and B5 was a fragment from −343 to −208 described in the deletion analysis of the 35S promoter in Fang et al. (1989) with an XhoI site at the 5' end and a SalI site at the 3' end. This was dimerized by ligation of the fragment at high concentration. The tetramer was formed by cleavage of the dimer construct with PstI followed by treatment with T4 DNA polymerase and then with SalI. The fragment was removed by cleavage with SalI, treatment with Klenow enzyme and then cleavage with XhoI. The ligation of these two molecules resulted in the tetramer described in FIGS. 8(k) and 8(m). It was subcloned into a derivative of pEMBL 13 at the SalI site and inserted into the expression vectors between the HindIII site (5') and the XhoI site (3').

The combination of B1 and a TGACG motif of CaMV35S (containing nucleotides −105 to −72) was synthesized as complementary oligonucleotides and inserted in the expression vectors as described above for B3 and B5.

The nucleotide sequences of the various subdomain constructs utlized in the invention are illustrated in FIGS. 8(a) through 8(m). Only the nucleotide sequence of the particular subdomain, domain A or the minimal promoter (−46 to +8) (whichever is appropriate) and associated linkers are shown. The linker sequences are necessary to incorporate the subdomain or subdomains into the construct, but do not affect the expression properties of the constructs. In all constructs a TATA box region fused to the subdomain or subdomains is necessary.

Transgenic Plants

Figure 3:
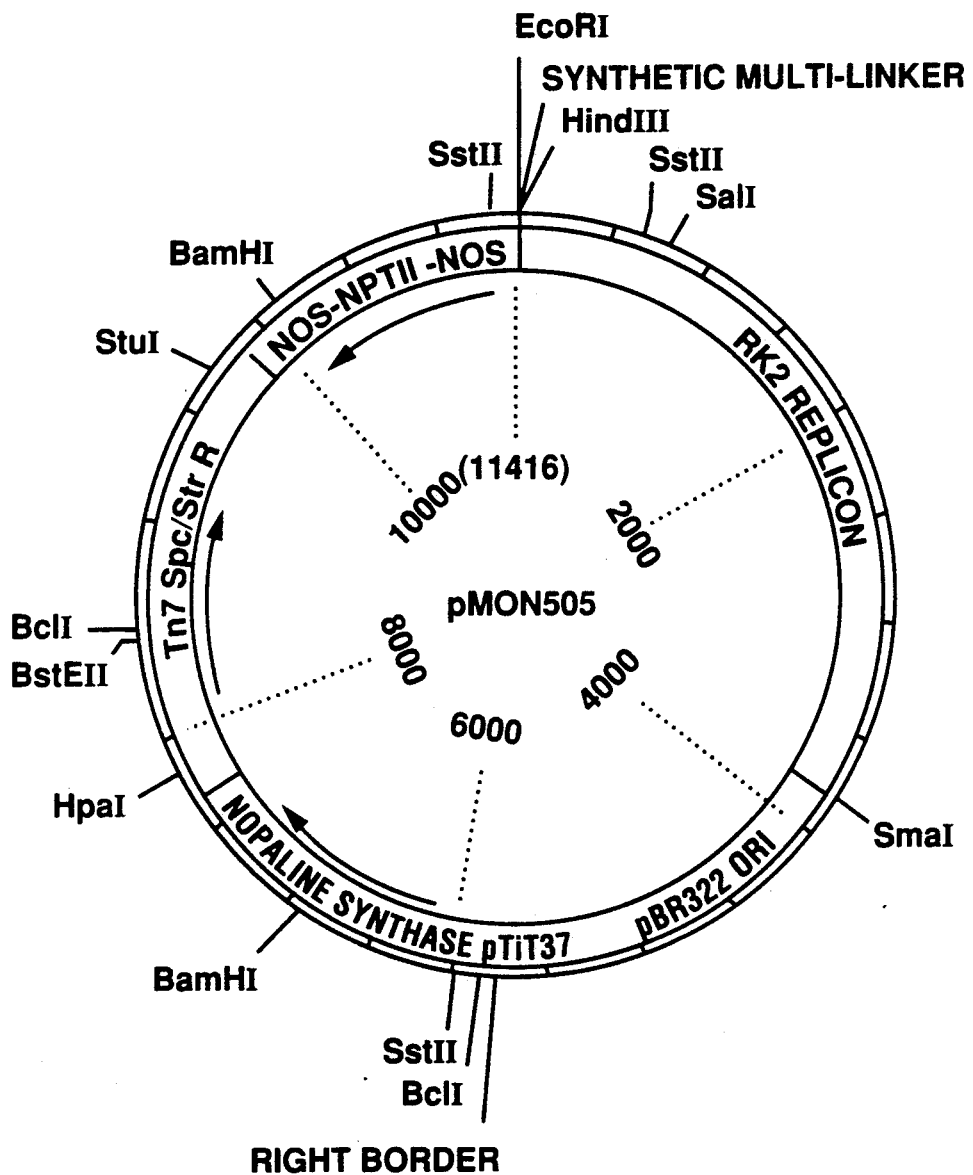
FIG. 3 illustrates a plasmid map of intermediate plant transformation vector pMON505.
Figure 4:
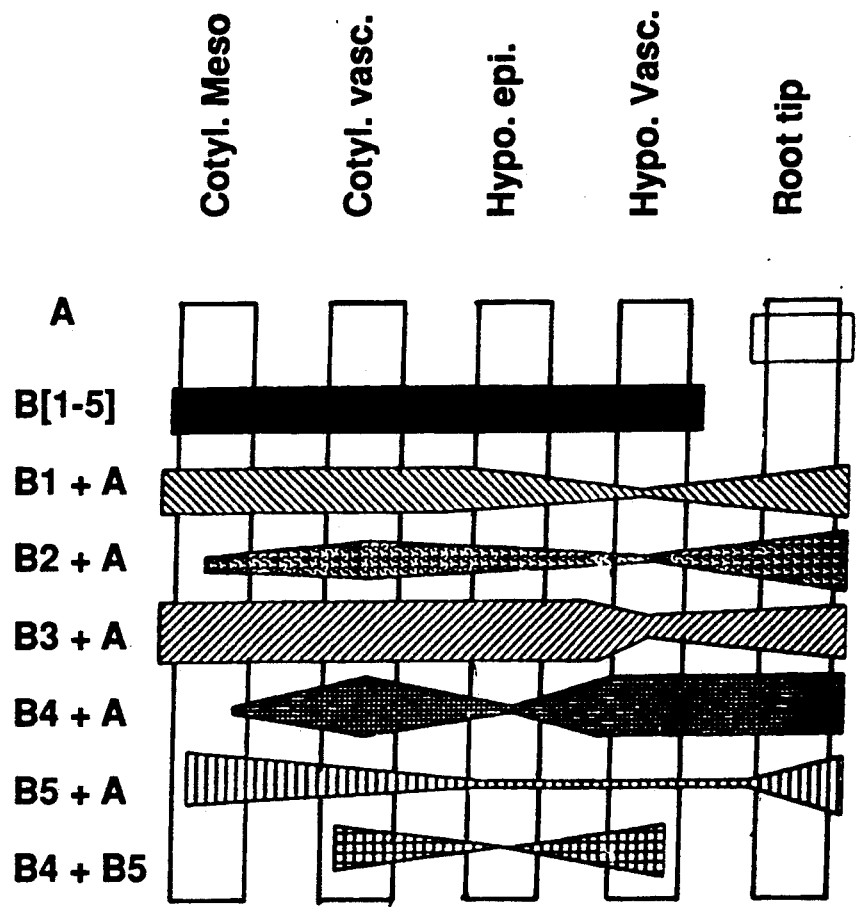
FIG. 4 is a schematic representation of expression patterns of subdomain constructs in seedling tissues.

The constructs were inserted into intermediate transformation vector pMON505 (FIG. 3) and mobilized into a "disarmed" Agrobacterium tumefaciens strain GV311SE by triparental mating (Rogers et al., 1986). Ex-conjugates were used to inoculate leaf discs of Nicotiana tobacum cv. SR1 and regenerated shoots were selected on a medium containing Kanamycin (200 μg/ml) (Rogers et al., 1986). After rooting, transgenic plantlets were transferred to soil and grown in a greenhouse. The primary transformants were allowed to self-fertilize and seeds were collected. For the studies on expression in seedlings and mature plants, seeds were sterilized and germinated on a media containing M.S. salts, 3% sucrose, 0.7% agar, 100 μg/ml Kanamycin and 500 μg/ml Carbenicillin. The seedlings were maintained at 26° C. in a cycle of 16 hours light, 8 hours dark. After approximately 21 days two seedlings from each transgenic plant were transferred to PLANTCONS (TM) containing the same media where they continued to grow under the same environmental conditions.

Histochemical Staining

Histochemical staining was performed as described in Jefferson (1987) with the following modifications. Mature seeds were deposited in a dense monolayer in adhesive (KRAZY GLUE TM) placed on a section from a carrot. The carrot section was attached to the block used for sectioning supplied with the Vibrotome (TM) sectioning device. Sections of 100 to 200 microns were cut with the VIBROTOME and placed directly in the histochemical substrate solution of 1 mM 5-bromo-4-chloro-3-indolyl glucuronide (X-Gluc) (Clontech) and 50 mM Sodium phosphate buffer (pH 7.0) on a microscope slide on which a thin bead of vaseline had been placed around the edge. The sections were incubated for 12 to 16 hours in a humidified chamber at 37° C. Coverslips were placed on the slides before viewing.

Six-day old seedlings were removed from petri dishes, placed directly in the X-Gluc solution and incubated as described above for the seeds. Ten and 17-day old seedlings were removed from petri dishes and placed in a small amount of X-Gluc solution on a microscope slide. The seedlings were then pressed with a second microscope slide. The pressed seedlings were then removed to a fresh microscope slide with X-Gluc solution and incubated as described above for seeds.

For the 7-10 week old plants, fresh sections were hand cut. Sections from root were placed directly in X-Gluc solution and incubated as described above. Sections from stem and leaf were incubated with the X-Gluc solution in 24-well microtiter dishes for 12-16 hours at 37° C., then cleared of chlorophyll by incubation for ten minutes in a solution of 5% formaldehyde, 5% acetic acid, and 20% ethanol, followed by incubation for two minutes in 50% ethanol, two minutes in 100% ethanol, and two washings in distilled water. The sections were then mounted on microscope slides for photography. Photomicrographs were taken with a Nikon Optiphot microscope using phase contrast optics.

Determination of Expression in Seed

Seeds from at least six independent transgenic plants containing the primary transformants were harvested. Fresh sections were made by imbedding the seeds in an adhesive and cutting 100 to 200 micron sections. The adhesive acts as a matrix and sections of embryos in all orientations are obtained. These sections were then incubated with the histochemical substrate.

In nearly all plants with constructs that contained domain A, staining in the radicle of the embryo and the radicle pole of the endosperm was observed. This is the expression pattern observed when domain A alone is present (Benfey et al., 1989). In plants containing subdomain B5 fused to domain A (B5+A or 4×B5+A) (This nomenclature is used throughout to denote the nature of the 35S portion of the construct: B5+A means a monomer of subdomain B5 is fused with domain A; 4×B5+A means that a tetramer of B5 is fused with domain A.), the same expression pattern as domain A was observed. This indicates that this subdomain does not confer any additional expression at this stage of development. For plants containing the other four subdomains fused to domain A staining in the cotyledon as well as in the radicle was observed.

Staining in the cotyledon is strongest with the tetramer of subdomain B3 (4×B3+A). Expression in the cotyledon is also quite strong with subdomain B1 (4×B1+A). For subdomains B2 and B4 (4×B2+A and 4×B4+A), expression is relatively weak in the cotyledon. In fact, for B2 the most common pattern is strong staining in the radicle. The same expression pattern is conferred for this subdomain in either orientation (4×B2+A or 4×B2r+A) (the r nomenclature indicates the placement of the subdomain in reverse orientation). The staining of 4×B4+A appears to be strongest in the center of the embryo. Monomers of the subdomains fused to domain A give qualitatively the same expression as the tetramers.

Seeds containing the combination of subdomains as a tetramer fused to the minimal promoter (4×(B4+B5)+ −46) exhibit staining principally in the cotyledon. When the tetramer is fused to domain A ((B4+B5)+A), expression is seen in the cotyledons and the radicle. No staining is observed in seeds containing the minimal promoter sequence alone.

The expression pattern of the entire domain B fused to the minimal promoter is identical to that described for domain B fused to the −72 to +8 promoter (Benfey et al., 1989). Expression is strong in the cotyledon and in the endosperm cells adjacent to the cotyledon. In some plants, light expression at the tip of the radicle is also observed. With subdomains B1, B4 and B5 when fused as tetramers to the minimal promoter, no expression in seed was detected in the plants analyzed. For the construct comprising 4×B3+ −46, expression in a broad region of endosperm tissue at the radicle pole and in a narrow region of the radicle tip of the embryo was observed. Subdomain B2 when fused with the minimal promoter (4×B2+ −46) confers expression that is restricted to the cells at the tip of the radicle and to a small region in the endosperm tissue at the radicle pole. At this seed stage of development, expression is consistently observed only with the subdomains B2 and B3 when fused with the minimal promoter, the combination of B4 and B5 fused with the minimal promoter (B4+B5), and with B1 when combined with the TGACG motif construct (B1+TG) when fused to the minimal promoter. For B4+B5, light to medium cotyledon expression with occasional expression in the radicle is detected. For 4×(B1+TG), expression is only observed in the radicle.

The expression patterns conferred by the subdomains in seed provide evidence for synergistic interactions. B1, B4 and B5, when fused to the minimal promoter (−46 to +8), confer no detectable expression in seed, but when fused to domain A, B1 and B4 confer expression beyond that observed for domain A alone. In addition, when B4 and B5 are combined, expression is observed when fused with the minimal promoter, when individually each confers no detectable pattern of expression. The fact that the entire domain B can confer strong expression in the cotyledon when fused to the minimal promoter also suggests that there are synergistic interactions between the subdomains. The presence of active cis-elements within the subdomains is indicated by the expression detected when the subdomains are fused to domain A.

Determination of Expression in Seedlings

Seeds were sterilized and germinated on media containing the antibiotics Kanamycin and Carbenicillin. Since all transformants contain the NPTII (II) coding sequence driven by the nopaline synthetase promoter from pMON505, selection for plants containing the transgene should occur in media that contains Kanamycin. Seedlings were harvested at 7, 10 and 17 days. The seedlings were prepared by pressing between glass slides in the presence of the histochemical substrate, then incubated with the substrate.

The ability of domain A to interact synergistically with other regulatory elements is particularly evident in the results of expression in seedlings. Expression has been observed in seedlings of the plants analyzed containing the subdomains B2, B3 and B4 when fused to the minimal promoter (−46 to +8). In contrast, when fused to domain A, four of the five subdomains confer expression beyond that observed when domain A alone is present. Subdomain B2 exhibits expression when found with domain A, but not significantly different from that of domain A alone. Furthermore, the combination of two subdomains (B4+B5) results in expression when fused with the minimal promoter. Expression from domain A alone is localized principally to the root in seedlings, with some expression in the stem apical region detectable after about ten days (Benfey et al., 1989). Expression from domain B when fused to the minimal promoter is strong in all cells of the cotyledon but is strong only in vascular tissue in the hypocotyl and root.

Expression from subdomain B1 (4×B1+A) is strong in the root and in the cotyledon of seedlings at 7, 10 and 17 days. Expression is variable in the hypocotyl, with light epidermal and cortex staining most frequently observed in younger seedlings. In older seedlings, expression in the hypocotyl is rarely detected.

Subdomain B2 (4×B2+A) confers strong expression in the root, but it is difficult to determine whether this differs significantly from the expression conferred by domain A alone.

Subdomain B3 in one copy (B3+A) or four copies (4×B3+A) confers nearly constitutive expression in young seedlings. In older seedlings expression is still strong in the root and cotyledon, but in the hypocotyl expression appears to be principally in the epidermis and trichomes.

Subdomain B4 when fused with domain A (B4+A) confers expression in the vascular tissue of the hypocotyl and cotyledons.

Subdomain B5 in one copy (B5+A) or four copies (4×B5+A) confers strong expression in the root of younger seedlings but only light expression in the cotyledon. The expression in the cotyledon appears to be principally in mesophyll cells. In the hypocotyl, some light epidermal expression is observed.

When fused to the minimal promoter, subdomains B2, B3 and B4 confer detectable expression. Expression is detected at the very tip of the root for subdomain B2. The staining appears to be principally in the root cap and in the meristematic region. No staining in the apical meristem region at the stem, nor in any other tissue has been observed. This staining pattern somewhat resembles that conferred by domain A. Domain A expression, however, is frequently observed in the apical meristem region of the stem. Furthermore, expression from domain A is usually less spatially restricted than that from 4×B2+ −46.

Subdomain B3, when fused with the minimal promoter, confers expression in cotyledons in 7-10 day old seedlings that is strongest at the base of the cotyledons. No expression in the root tip is detectable; however in older seedlings some expression in what appears to be root cortex is seen.

Expression from subdomain B4 when fused with the minimal promoter was observed at the 17 day stage of the seedling in the vascular tissue at the shoot apex. No expression was detected in seedlings at any stage with subdomains B1 or B5.

The combination of subunits B4 and B5 as a tetramer fused to the minimal promoter, 4×(B4+B5)+ −46, gives reproducible expression in the vascular tissue of the hypocotyl and leaf. The monomer, B4+B5, gives the same pattern of expression to that of subdomain B4. When fused to domain A (4×(B4+B5)+A) expression is detectable in the vascular tissue of the hypocotyl and cotyledon as well as in mesophyll cells of the cotyledon. Also, the combination of B1 and one TGACG motif 4×(B1+TG) gives expression that varies among independent transformants. In some plants, weak root cortex expression is evident. In others, expression is detectable in the region around the shoot apex and in the mesophyll cells of the cotyledon.

At this seedling stage of development, it is possible to detect expression conferred by each of the subdomains. However, subdomains B1 and B5 appear to require an auxiliary function supplied by domain A to confer detectable expression. The expression patterns resulting from the fusion of individual subdomains to domain A range from nearly constitutive expression (B3) to principally vascular expression (B4) or principally mesophyll expression (B5) along with the root tip expression conferred by domain A alone. It is interesting to note that neither subdomain B4 or B5 when fused to the minimal promoter (−46 to +8) gives detectable expression in the vascular tissue of 7-10 day seedlings. When the two subdomains are combined, however, expression in the vascular tissue of the cotyledon, hypocotyl and root is observed. Based on these results, B4 and B5 may interact synergistically to give expression in the absence of domain A. The fact that the expression pattern of (B4+B5)+ −46 is very similar to that of B4+A (except for the root expression conferred by domain A) suggests that subdomain B5 may be supplying the auxiliary function required by subdomain B4 for expression. In the same way, the expression pattern of the entire domain B in the absence of domain A can be explained either by suggesting that important sequence motifs were interrupted when the subdomains were isolated or that there are synergistic interactions among the subdomains.

Determination of Expression in Developed Plants

The plants were maintained in tissue culture and sections were cut at seven to ten weeks after germination. Expression was analyzed in sections from younger and older leaves, from upper and lower stems, and from roots. After initially analyzing expression from the progeny of the primary transformants, additional primary transformants were generated containing constructs for which less than six $R_1$ plants were obtained. These were constructs containing B1, B3 and B4 fused to the minimal promoter, respectively. For these plants, cuttings from the primary transformants were analyzed.

In the presence of domain A, each subdomain confers a different expression pattern beyond that conferred by domain A alone. Domain A alone confers weak expression in the vascular tissue of leaf, in the vascular parenchyma and phloem of stem, and relatively strong expression in the cortex and meristematic region of root (Benfey et al., 1989). In addition, expression from domain A is particularly strong in lateral roots and in the pericycle tissue at the site of lateral root formation (Benfey et al., 1989). Domain B fused to the minimal promoter confers nearly constitutive expression in leaf and stem, while in root, expression is principally in vascular tissue with expression occasionally observed in cortex and root cap.

Subdomain B1 (4×B1+A) gives nearly constitutive expression in leaf. In stem, expression is somewhat weaker and found principally in the vascular parenchyma, pith and cortex. Root expression resembles that from domain A alone, with strong pericycle and some additional cortex expression.

Subdomain B2 as a tetramer (4×B2+A) confers expression principally in the vascular tissue in leaf. In stem, the expression is almost exclusively in vascular tissue that appears to be sieve tube elements. In root, expression in vascular tissue as well as cortex and meristematic tissue is observed. The same expression pattern results when the tetramer is in either orientation.

Subdomain B3 (B3+A or 4×B3+A) gives strong, nearly constitutive expression in leaf and stem. Expression in trichomes is particularly evident in leaf. In root, expression is the same as that with domain A alone, except that enhanced cortex expression is observed.

Subdomain B4 (B4+A or 4×B4+A) confers weak vascular expression in leaf that is difficult to distinguish from expression conferred by domain A alone. In the upper stem, however, strong expression in the vascular parenchyma is observed. In lower stem, expression seems to be principally in the phloem. In root, expression in vascular tissue is sometimes detected, in addition to expression typical of that conferred by domain A.

Subdomain B5 (B5+A or 4×B5+A) confers weak vascular and mesophyll expression in leaf. In stem, expression is principally in the vascular parenchyma with some expression in pith and cortex. The expression pattern in root is similar to that conferred by domain A.

Figure 5:
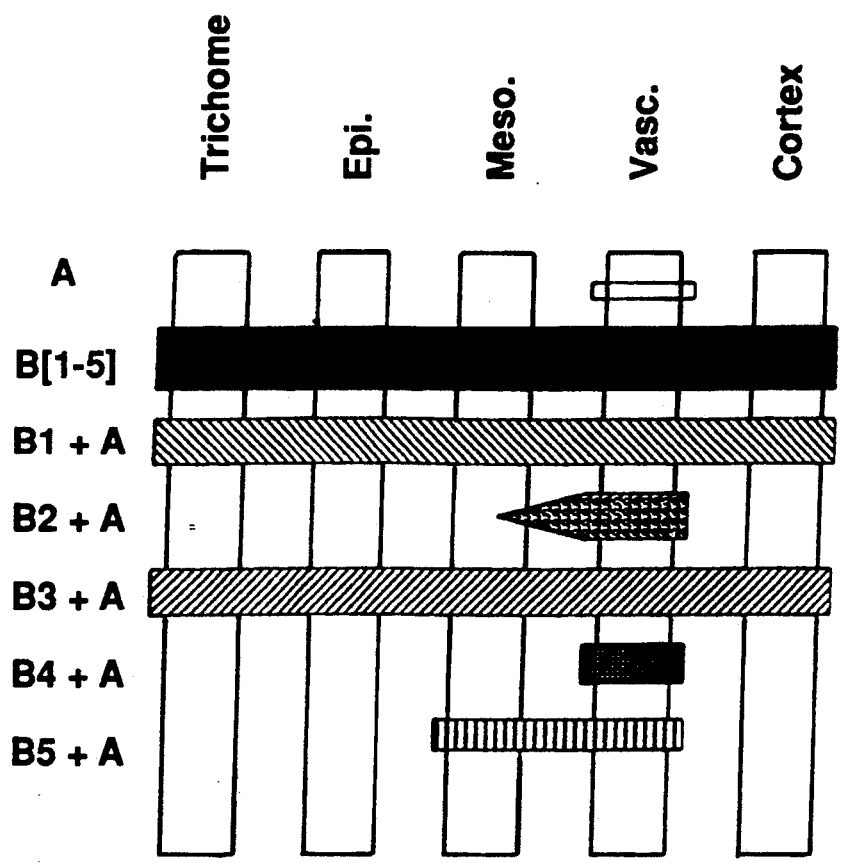
FIG. 5 is a schematic representation of expression patterns of subdomain constructs in leaf tissues.
Figure 6:
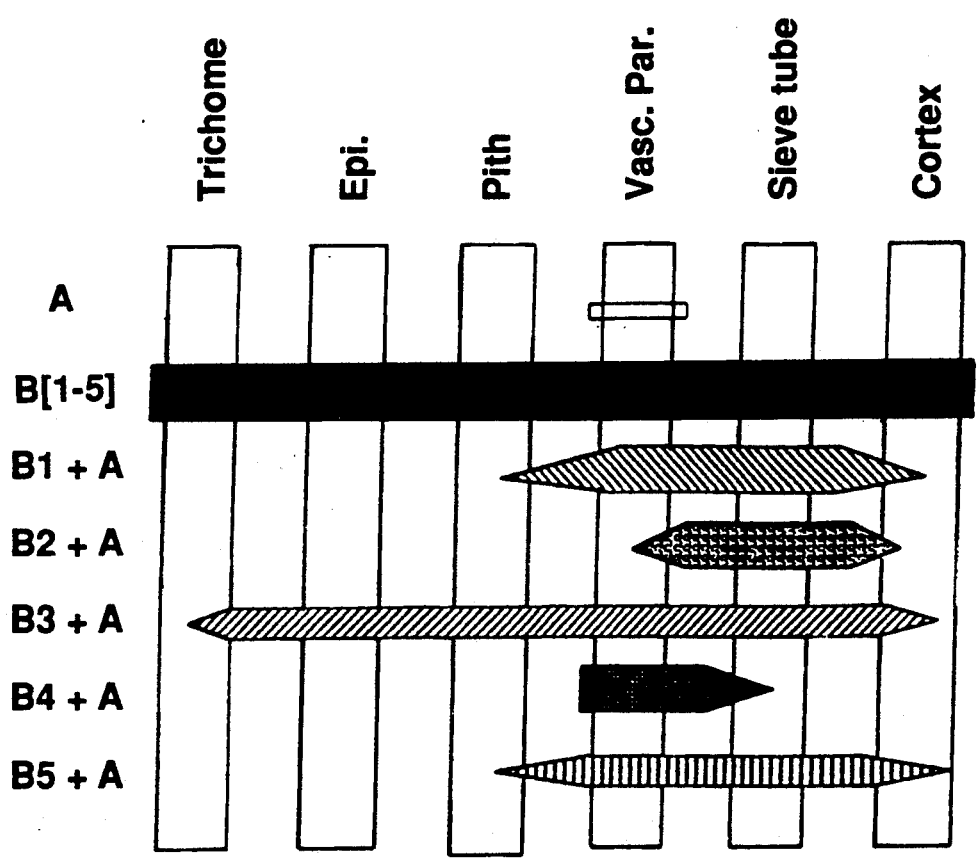
FIG. 6 is a schematic representation of expression patterns of subdomain constructs in stem tissues.

The expression patterns conferred by the five subdomains in the presence of domain A can be divided into two classes. Two subdomains, B2 and B4, give principally vascular expression in leaf and stem (FIGS. 5 and 6). Three subdomains, B1, B3 and B5, give expression in tissues in addition to vascular tissue in leaf and stem (FIGS. 5 and 6). Within these classes there appear to be finer distinctions. In the first class, expression from B2 appears to be stronger in sieve tube elements in the stem while expression from B4 appears to be stronger in vascular parenchyma (FIG. 6). In addition, in the case of B4, overall expression in the stem seems to be stronger in younger than in older stem tissue. In the second class, expression from B3 is virtually constitutive in leaf and stem, expression from B1 is nearly constitutive in the leaf, but relatively weak in the stem, and expression from B5 is stronger in the stem than in the leaf.

In mature plants, four of the five subdomains (B2, B3, B4 and B5) confer distinct expression patterns when fused with the minimal promoter. For subdomain B1 expression in only one $R_0$ plant was detected. The ability of the subdomains to interact synergistically with domain A is evidenced by the detection of expression in tissues that show no expression with either the isolated subdomain or domain A alone.

In longitudinal sections of the stem apex, weak expression from B1 was detected in only one $R_0$ plant at the nodes of the apex when fused with the minimal promoter sequence. When fused to domain A, stronger expression in this region is reproducibly detected. Expression from B2 with the minimal promoter sequence is detected only in isolated cells found between the pith and the xylem. With domain A, expression is observed in cells that appear to make up the network of sieve tubes. Expression from B3 fused with the minimal promoter sequence in the $R_0$ plants is in nearly all cells of the apex, with the strongest expression at the sites of emerging leaves. In the $R_1$ plants analyzed, expression was detected principally at the site of emerging leaves. In combination with domain A, expression from B3 is detected in most cells throughout the stem apex. Expression from B4 when fused with the minimal promoter sequence is detected principally in vascular parenchyma cells. The same expression pattern is observed in the $R_1$ plants and in the primary transformants. When combined with domain A, expression appears to be greatly enhanced in cells of the vascular parenchyma. Subdomain B5 plus the minimal promoter sequence confers only weak expression in cells that are just below the apical meristem. Some enhancement of expression in this region is observed with the addition of domain A.

In the stem apex, domain A confers weak expression in cells that flank the apex, and in some cells that appear to be part of the apical meristem. Domain B confers strong expression in nearly all cells of the stem apex. The combination B4+B5 as a monomer fused to the minimal promoter sequence gives expression that is very similar to that of B4, staining principally in the vascular parenchyma. As a tetramer, B4+B5 plus the minimal promoter sequence shows enhanced expression in the vascular parenchyma tissue. When fused to domain A the monomer of B4+B5 confers strong expression in vascular tissue as well as some expression in pith and cortex.

Transverse sections through the upper and lower stem revealed expression in certain tissues not detected at the apex. In the lower stem of the $R_0$ plant, B1 plus the minimal promoter sequence confers weak expression in vascular tissue at the leaf trace. When fused to domain A, weak expression in cortex and pith as well as in vascular tissue is frequently detected. The highly restricted expression pattern of B2 with the minimal promoter sequence is seen in stem sections where only a single cell type stains. These cells appear to be part of the phloem elements and may be sieve tube cells at a particular stage of development. In combination with domain A, strong expression in phloem elements is observed. In the $R_0$ plants, B3 when fused with the minimal promoter sequence confers expression in nearly all cell types in lower stem, with particularly strong expression in the vascular tissue at the leaf trace. Even in the $R_1$ plants in which B3 gives very little expression in upper stem, in lower stem relatively strong expression in vascular tissue at the leaf trace where expression is also detected in the cells at the stem/leaf junction. B3 in combination with domain A, confers expression in most cells of the stem. Subdomain B4 with the minimal promoter sequence confers weak expression in what appears to be the developing vascular tissue including vascular parenchyma and phloem element cells. This expression is strongly enhanced when B3 is combined with domain A. Expression from subdomain B5 with the minimal promoter sequence is only detected in a small set of cells within buds emerging from the stem. Fusion to domain A results in expression in the entire bud as well as in cells at the stem/leaf junction.

Domain A alone confers weak expression in vascular parenchyma and phloem cells particularly at the leaf trace. The intact B domain gives strong expression in nearly all cells of the stem. As a monomer, the combination B4+B5 gives expression in vascular parenchyma and phloem cells which is similar to the expression of B4 alone, when fused to the minimal promoter sequence. Expression from the tetramer appears to be somewhat enhanced in the same cells, while expression from the monomer fused to the A domain is observed in some pith and cortex cells in addition to strong expression in the vascular parenchyma and phloem.

Expression in leaf tissue was observed from B1 in the primary transformant plant only in young leaves. Mesophyll and vascular cells in the lamina of the leaf show faint staining. B1 in combination with domain A reproducibly gives expression in most cells of the leaf. As in the stem, B2 plus the minimal promoter sequence confers expression only in isolated cells within the phloem elements in the leaf. When fused to domain A, B2 gives strong expression in phloem elements. In the $R_0$ plants, B3 fused to the minimal promoter sequence gives different expression patterns in young leaves and old leaves. In young leaves expression is principally in the lamina and is particularly strong in mesophyll and trichome cells. In the midrib, B3 confers expression principally in the trichomes. In older leaves, expression is detected in the vascular tissue of the midrib and only faint staining of mesophyll and trichome cells in the lamina is observed. In $R_1$ plants, only weak expression from B3 in vascular tissue of the midrib in older leaves was detected. When combined with domain A, strong expression in nearly all cell types of the leaf is consistently observed. Strong expression in all cells is seen in both young and old leaves. Subdomain B4 with the minimal promoter sequence confers expression in vascular parenchyma cells of the leaf. Enhancement of expression in these cells appears to occur when B4 is combined with domain A. In one plant containing B5 with the minimal promoter sequence, weak expression in mesophyll tissue was detected. When combined with domain A, weak expression in mesophyll and vascular tissue is often observed.

Domain A confers very weak expression in vascular tissue of the leaf. Domain B alone gives expression in nearly all cells of the leaf. The combination B4+B5 as a monomer or as a tetramer fused with the minimal promoter sequence confers expression in vascular parenchyma and phloem cells similar to that found with the tetramer of B4. When fused to domain A the monomer of B4+B5 gives strong expression in the vascular tissue. The cells immediately adjacent to the vascular elements also stain.

In root tissue B1 plus the minimal promoter sequence gives weak expression in phloem tissue and occasionally in cells that appear to be part of the root cap in the only plant that shows any expression. Expression from domain A alone is principally observed in the meristematic region and cortex of the root tip as well as in the pericycle (see Benfey et al., 1989). Less frequently, some expression has been detected in the root cap, in root hairs, and in cortex. No expression has been detected in vascular tissue. Expression from B1+A usually resembles that of domain A alone with expression at the meristematic region of the tip and in the pericycle. B2 plus the minimal promoter sequence confers strong expression that appears to be restricted to the cells in the root cap, as well as faint expression in the root hairs closest to the root tip. No expression is detected in other root tissue. When fused to domain A, however, expression in phloem tissue is observed as well as expression in the root tip and pericycle characteristic of domain A. Subdomain B3 when fused with the minimal promoter sequence confers expression principally in root cortex as detected in the primary transformants. Weak expression in phloem tissue was also occasionally detected. In the $R_1$ plants only weak expression in some cortex cells was occasionally observed. When combined with domain A, expression in cortex in addition to expression characteristic of domain A was frequently observed. No expression in root from B4 in the $R_1$ or in the primary transformants when combined with the minimal promoter sequence was detected. When combined with domain A expression in phloem tissue is reproducibly observed. For B5 combined with the minimal promoter sequence also, no expression was detected in the root. In combination with domain A, there was occasionally some apparent enhancement of expression in cortex tissue, although this could be attributed to domain A alone.

Domain B alone confers expression in vascular tissue in the root and less frequently in cells that appear to be part of the root cap. The combination B4+B5 plus the minimal promoter sequence as a monomer gives no expression, but as a tetramer consistently confers expression in phloem tissue of the root. When fused to domain A, B4+B5 confers expression in most of the cells of the vascular cylinder. In eleven plants containing the TATA vector alone no staining in any tissue was detected.

The present invention provides evidence that the ability of domain B to function when fused to the minimal promoter is due to synergistic interactions among the cis-elements within domain B.

In the mature plant, expression is detected from four of the five subdomains when fused to the minimal promoter. Subdomain B1 reproducibly confers expression only in combination with domain A. Three of the expression patterns of the individual subdomains are restricted in cell type. The B2 pattern of expression is in cells of the root cap, root hair, and a single vascular cell type. Evidence for synergistic interactions comes from the combination of all of the subdomains with domain A which generates expression that is detectable in tissues that do not show expression with the isolated subdomain or with domain A. The combination of subdomains B4+B5 as a monomer with the minimal promoter sequence gives expression in most tissues that is similar to that of B4 as a tetramer with the minimal promoter sequence indicating that multimerization is not a necessary condition to obtain this expression pattern. Additionally, the tetramer B4+B5 fused to the minimal promoter sequence confers expression in root phloem tissue where neither of the isolated subdomains show expression in this tissue.

By monitoring the expression patterns conferred by the subdomains in different tissues and throughout development, differences in expression were detected that would have been obscured had expression in a single organ been analyzed. Analysis of the expression patterns conferred by the isolated subdomains reveals expression that is quite restricted in cell type. Subdomain B4 gives detectable expression only in vascular tissue. Expression appears to be principally in the immature vascular cells of the vascular parenchyma and phloem. The ability of B4 to confer expression in developing vascular tissue is also evident in the finding that in combination with domain A or with B5 expression is consistently observed in vascular tissue in the hypocotyl of young seedlings. Subdomain B2 also confers expression in cells that appear to be part of the vascular tissue. In this case, however, expression is only detected in isolated cells that appear to be a constituent part of the phloem. The identity of these cells becomes more definite when expression from B2 fused to domain A is observed. The interconnecting pattern of staining cells is characteristic of sieve tubes. From these two observations it appears that B2 alone directs expression in sieve tube cells at a particular stage of development. Comparison of the expression patterns of B4 and B2 suggests that the former confers expression primarily in immature vascular tissue and the latter gives expression in more mature cells of the vascular elements. This result indicates that within the B domain there are modules that confer complementary expression patterns. Expression from B2 is not restricted to cells within the phloem elements. Expression in two other tissues, the root cap and root hairs, is also detected.

The three other subdomains are able to confer expression in non-vascular tissue of the leaf and stem. For subdomains B1 and B5 this is only readily apparent when they are fused to domain A. In the absence of domain A, expression from B5 is restricted to a very few cells in the stem apex and in young buds, while in one plant the isolated subdomain B1 is able to confer expression in mesophyll tissue in young leaves. The expression pattern of subdomain B3 is the most complex. In young leaves, expression is strong only in non-vascular tissues. In older leaves, however, the situation is reversed, with strong staining in vascular tissue and only weak staining in other tissues. In stem, expression in nearly all cells is observed. When combined with domain A, nearly all cells show staining in both young and old leaves. The complexity of the expression pattern conferred by B3 suggests there may be several active cis-elements within this subdomain. The presence of more than one active cis-element within this subdomain may also account for the dramatic changes in the expression pattern throughout development. For example, in the seed there is strong expression in endosperm tissue at the radicle pole, as well as weak expression in the radicle of the embryo, while in young seedlings no expression in the root is detected.

Comparison of the expression patterns conferred by these three subdomains indicates that there is some functional redundancy among the subdomains that make up the 35S enhancer. This redundancy is generally restricted, however, to a particular organ at one stage of development. When the expression patterns are compared in other organs and throughout development it becomes clear that substantial differences exist among the patterns conferred by the subdomains.

The cell specific expression patterns conferred by these subdomains can serve as useful markers for cells at particular developmental stages. For example, expression from B2 and B4 could be useful in studies of vascular development. For studies of root development useful markers include expression from B2 in the root cap, domain A in the pericycle and meristematic region, B3 in cortex, and B4+B5 in vascular tissue. These restricted expression patterns raise the possibility that the factors that interact with these sequences regulate endogenous plant genes that are involved in some aspect of development.

Figure 7:
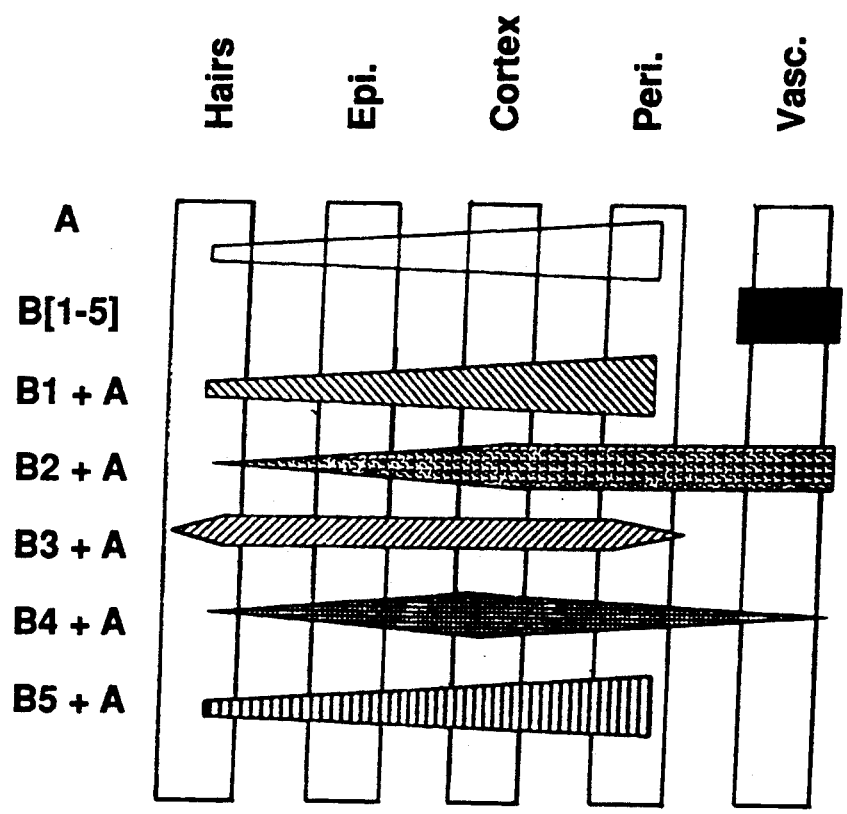
FIG. 7 is a schematic representation of expression patterns of subdomain constructs in root tissues.
Figure 9:
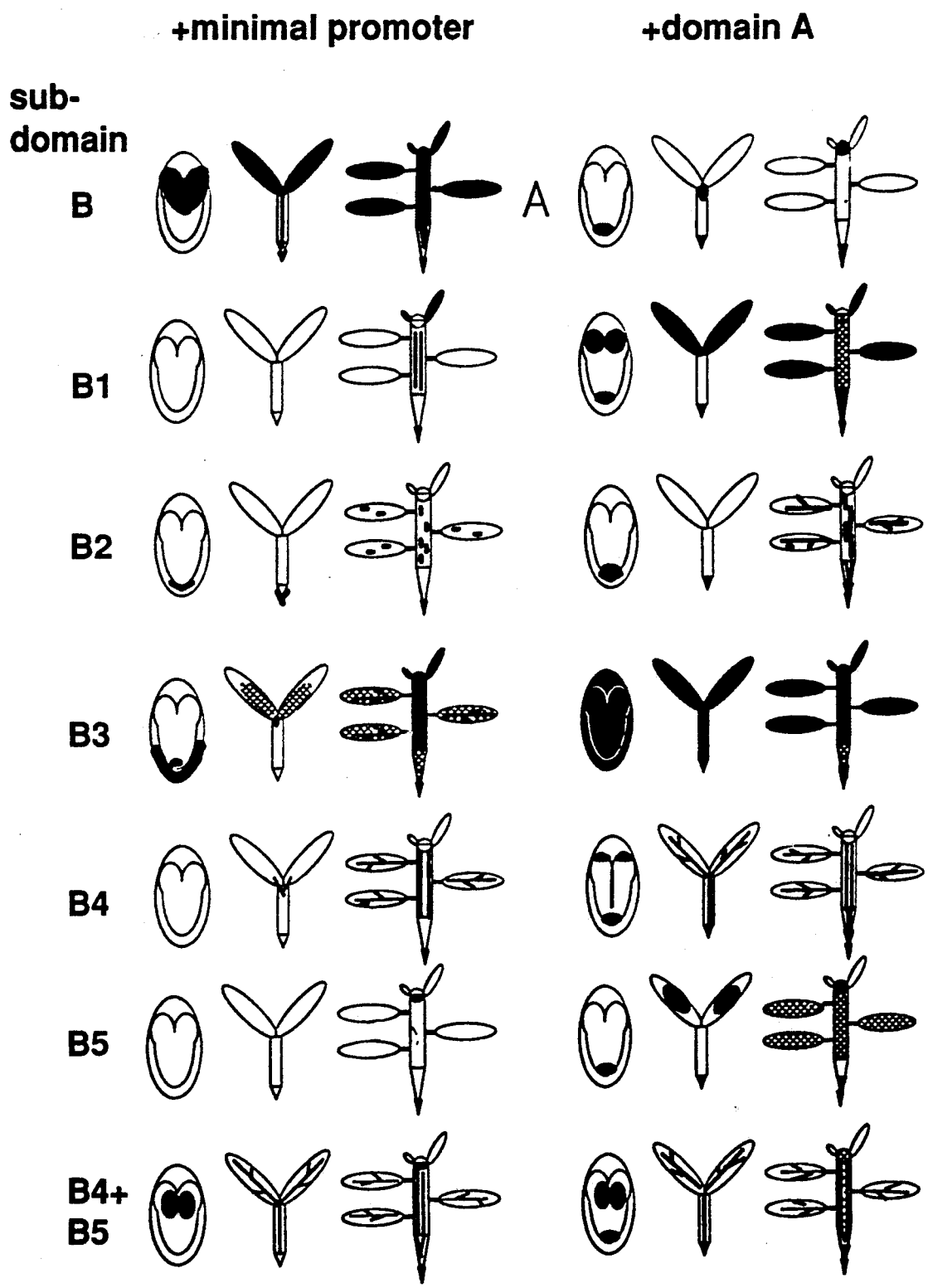
FIG. 9 is a schematic illustration of the expression patterns of the individual subdomains observed in seeds, seedlings and plants when fused with the minimal promoter or domain A.

The expression pattern conferred by B1 (as a tetramer) or B3 (as a monomer or tetramer) fused to domain A is virtually constitutive in leaf. In stem, however, B3 appears to be more active than B1. The tissue in which expression is consistently absent with either of these subdomains is vascular tissue in root (FIG. 7). Also in seedlings, expression in the vascular tissue of the hypocotyl is rarely detected with B1. It appears, therefore, that subdomains B1 and B3 confer expression patterns that are complementary to those of subdomains B4 and B5 (FIGS. 4–7).

The use of histochemical localization to detect cell specific expression patterns is not without potential problems. Differences in cell size and metabolism as well as penetration of the substrate into the cell can contribute to differences in staining intensity (Jefferson et al., 1987). The variety of staining patterns that was observed is an indication that clearly different patterns can be detected by these methods.

Striking variation in the staining pattern among independent transgenic plants that contained the intact 35S promoter has previously been noted (Benfey and Chua, 1989). It has been postulated that this variation indicated that the 35S promoter might have a modular organization with elements that confer tissue specific expression being differentially affected by chromosomal position (Benfey and Chua, 1989). One prediction of this model is that when cis-elements are isolated, variation in expression should be principally quantitative. This is supported by the results of this invention.

It is concluded that the 35S enhancer has a modular organization. The constitutive nature of the enhancer derives from the presence of modules that can confer complementary expression patterns, examples of which are B3 and B4. There also appears to be a degree of functional redundancy, at least in certain tissues, for example, expression from B1 or B3 in leaf. It appears likely that there are synergistic interactions among subdomains so that the expression pattern conferred by the entire enhancer is different from the sum of the expression patterns of the individual modules. The apparent synergistic interaction of subdomains B4 and B5 provides clues as to the potential interaction of the factors that bind sequences within the subdomains. The fact that subdomain B4 confers vascular expression in seedlings in the presence of domain A or subdomain B5, suggests that the factors that bind to all three sequences are present in vascular tissue. However, subdomain B5 fused to domain A does not confer vascular expression. This suggests there may be a qualitative difference in the factors that bind these sequences, or that there are differences in abundance.

It has been found that the 35S enhancer has two domains and five subdomains. Within domain A, a sequence motif termed as-1 that binds a factor, ASF-1, has been identified (Lam et al., 1989). Within subdomain B1, a sequence motif as-2 has been identified that competes with sequences from the chlorophyll a/b binding protein (Cab) gene for binding of a factor ASF-2 (E. Lam in preparation). This factor is found in nuclear extracts from leaf but not from root.

Determination of the expression patterns of the subdomains as disclosed in this invention should allow characterization of the sequence motifs within each subdomain responsible for expression. It is quite possible that within some subdomains there are more than one active sequence motif. In addition, the localization of expression within specific tissues, provides clues as to the likely presence of higher concentrations of active binding factors.

Furthermore, the identification of tissue or cell-type specific promoters is useful in providing the plant molecular biologist with the ability to direct the expression of a desired gene to a particular tissue or cell-type for better specificity of action. The subdomains identified may be used in conjunction with any gene desired and in any plant species.

REFERENCES

Benfey, P. N. and Chua, N. H. (1989) *Science* 244:174–181.
Benfey, P. N., Ren, L. and Chua, N. H. (1989) *EMBO J.*, 8:2195–2202.
Fang, R. X., Nagy, F., Sivasubramaniam, S. and Chua, N. H. (1989) *Plant Cell* 1:141–150.
Horsch, R. B. and Klee, H. J. (1986) *Proc. Natl. Acad. Sci. U.S.A.*, 83:4428–4432.
Jefferson, R. A., Kavanagh, T. A. and Bevan, M. W. (1987) *EMBO J.* 6:3901–3907.
Jensen, J. S., Marcker, K. A., Otten, L. and Schell, J. (1986) *Nature* 321:669–674.
Katagiri, F., Lam, E. and Chua, N. H. (1989) *Nature*, 340:727–730.
Kay, R., Chan, A., Daly, M. and McPherson, J. (1987) *Science* 236:1299–1302.
Lam, E., Benfey, P. N., Gilmartin, P., Fang, R. X. and Chua, N. H. (1989) *Proc. Natl. Acad. Sci. U.S.A.*, 86:7890–7894.
Nagy, F. Boutry, M., Hsu, M. Y., Wong, M. and Chua, N. H. (1987) *EMBO J.*, 9:2537–2542.
Odell, J. T., Nagy, F. and Chua, N. H. (1985) *Nature* 313:810–812.
Rogers, S. G., Horsch, R. B., and Fraley, R. T. (1986) *Methods in Enzymology*, 118:627–640.
Sanders, P. R., Winter, J. A., Barnason, A. R., Rogers, S. G. and Fraley, R. T. (1987) *Nuc. Acids Res.* 4:1543–1558.

What we claim is:

1. An isolated DNA segment consisting of the nucleotide sequence:

5'-CGACCAGCAT CGTGGAAAAA GAA-GACGTTC CAACCACGTC TTCAAAGC-3'.

2. A DNA sequence consisting of a first nucleotide sequence:

5'-CGAGGAGCAT CGTGGAAAAA GAA-GACGTTC CAACCACGTC TTCAAAGC-3' and a second nucleotide sequence corresponding to domain A of the CaMV35S promoter coupled to said first nucleotide sequence by means of a synthetic multilinker.

3. A DNA sequence consisting of a first nucleotide sequence:

5'-CATCGTTGAAG ATGCCTCTGC CGACAGTGGT

CCCAAAGATG GACCCCCACC CAC-3' and a second nucleotide sequence corresponding to domain A of the CaMV35S promoter coupled to said first nucleotide sequence by means of a synthetic multilinker.

4. A DNA sequence consisting of a first nucleotide sequence:

5'-ATTCC ATTGCCC AGCTATCTGT CACTTTATTG

TGAAGATAGT GGAAAAGGAA

GGTGGCTCCT ACAAATGCCA TCATTGCGAT

AAAGGAAAGG CC-3' and a second nucleotide sequence corresponding to domain A of the CaMV35S promoter coupled to said first nucleotide sequence by means of a synthetic multilinker.

5. A DNA sequence consisting of a first nucleotide sequence:
5'-TGAGACTTTT CAACAAAGGG TAA-TATCCGG AAACCTCCTC GGATT-3' and
a second nucleotide sequence corresponding to domain A of the CaMV35S promoter coupled to said first nucleotide sequence by means of a synthetic multilinker.

6. An isolated DNA segment consisting of the nucleotide sequence:

5'-CATCGTTGAAG ATGCCTCTGC CGACAGTGGT

CCCAAAGATG GACCCCCACC CAC-3'.

7. An isolated DNA segment consisting of the nucleotide sequence:

5'-ATTCC ATTGCCC AGCTATCTGT CACTTTATTG

TGAAGATAGT GGAAAAGGAA

GGTGGCTCCT ACAAATGCCA TCATTGCGAT

AAAGGAAAGG CC-3'.

8. An isolated DNA segment consisting of the nucleotide sequence:

5'-TGAGACTTTT CAACAAAGGG TAA-TATCCGG AAACCTCCTC GGATT-3'.

9. A DNA sequence consisting of a first nucleotide sequence
5'-CGAGGAGCAT CGTGGAAAAA GAA-GACGTTC CAACCACGTC TTCAAAGC-3'
and
a second nucleotide sequence corresponding to the minimal promoter region of the CaMV35S promoter coupled to said first nucleotide sequence by means of a synthetic multilinker.

10. A DNA sequence consisting of a first nucleotide sequence

5'-CATCGTTGAAG ATGCCTCTGC CGACAGTGGT

CCCAAAGATG GACCCCCACC CAC-3' and
a second nucleotide sequence corresponding to the minimal promoter region of the CaMV35S promoter coupled to said first nucleotide sequence by means of a synthetic multilinker.

11. A DNA sequence consisting of a first nucleotide sequence

5'-ATTCC ATTGCCC AGCTATCTGT CACTTTATTG

TGAAGATAGT GGAAAAGGAA

GGTGGCTCCT ACAAATGCCA TCATTGCGAT

AAAGGAAAGG CC-3' and
a second nucleotide sequence corresponding to the minimal promoter region of the CaMV35S promoter coupled to said first nucleotide sequence by means of a synthetic multilinker.

12. A DNA sequence consisting of a first nucleotide sequence
5'-TGAGACTTTT CAACAAAGGG TAA-TATCCGG AAACCTCCTC GGATT-3' and
a second nucleotide sequence corresponding to the minimal promoter region of the CaMV35S promoter coupled to said first nucleotide sequence by means of a synthetic multilinker.

* * * * *